United States Patent [19]

Vormbrock

[11] Patent Number: 5,258,315

[45] Date of Patent: Nov. 2, 1993

[54] PROCESS AND COMPOSITION FOR THE REMOVAL OF TURBIDITY FROM BIOLOGICAL FLUIDS

[75] Inventor: Rolf Vormbrock, Darmstadt, Fed. Rep. of Germany

[73] Assignee: Merck Patent Gesellschaft mit beschrankter Haftung, Darmstadt, Fed. Rep. of Germany

[21] Appl. No.: 712,379

[22] Filed: Jun. 10, 1991

[30] Foreign Application Priority Data

Jun. 9, 1990 [DE] Fed. Rep. of Germany ....... 4018502

[51] Int. Cl.$^5$ .................. G01N 33/52; G01N 33/66
[52] U.S. Cl. ..................... 436/174; 436/17; 252/174.22; 252/408.1
[58] Field of Search ............... 436/174, 17; 252/408, 252/174.22

[56] References Cited

U.S. PATENT DOCUMENTS

| | | | |
|---|---|---|---|
| 3,864,472 | 2/1975 | Pensak et al. | 424/54 |
| 3,869,308 | 3/1975 | Graham | 428/424.4 |
| 4,282,001 | 8/1981 | Klose et al. | 436/174 |
| 4,369,250 | 1/1983 | Gindler | 435/18 |
| 4,510,239 | 4/1985 | Miller | 435/7 |
| 4,621,049 | 11/1986 | Wang | 435/14 |
| 5,041,390 | 8/1991 | Skov et al. | 436/527 |

*Primary Examiner*—James C. Housel
*Assistant Examiner*—David Redding
*Attorney, Agent, or Firm*—Millen, White, Zelano & Branigan

[57] ABSTRACT

A process and a composition for the removal of turbidity from biological fluids by the addition of surface-active agents, which is characterized in that the surface-active agents used are a. an alkyldimethylbenzylammonium compound,
b. a polyethoxylated triester of sorbitan or sorbiol with long-chain fatty acids,
c. optionally, an amphoteric surfactant,
d. optionally, a buffer, and
e. optionally, a salt in aqueous solution.

21 Claims, No Drawings

PROCESS AND COMPOSITION FOR THE REMOVAL OF TURBIDITY FROM BIOLOGICAL FLUIDS

BACKGROUND OF THE INVENTION

The invention relates to a process and a composition for the removal of turbidity from biological fluids using surface-active substances.

In the analysis of biological fluids, turbidity caused by lipophilic substances present in the specimen often presents a problem for the photometric measurement of constituents of the specimen.

In the clinicochemical examination of serum or plasma, various attempts have therefore been made to eliminate this interference. Examples of known processes are extraction of the specimen with a water-immiscible organic liquid, precipitation of the lipid particles present in the specimen or solubilisation of the lipids. Extraction and precipitation methods require a step for preparation of the specimen and result in a change in volume of the specimen, so these techniques are unsuitable for a reliable routine analytical procedure.

For solubilisation of the lipids, surfactant mixtures have been used, the composition and action of which are described in detail in European patent 130 537. In most cases, beyond a certain triglyceride concentration and when a certain specimen/reagent ratio is exceeded, these reagents are no longer effective, so the turbidity of the specimen leads to false measurement values despite the additives in the reagent. The process described in European patent 130 537 is based on a combination of three surfactants and led to clarification of the specimen within 10 minutes, even for a high triglyceride concentration and high proportion of specimen to reagent by volume.

Thus, the art lacks a process and a simple composition for the removal of turbidity from biological fluids which effect complete dissolution of the lipid particles within a short time, even for a high proportion of specimen to reagent, without interfering with the detection reaction.

SUMMARY OF THE INVENTION

The present invention provides a process for the removal of turbidity from biological fluids by the addition of surface-active agents, which is characterised in that the surface-active agents used are
a. an alkyldimethylbenzylammonium compound,
b. a polyethoxylated triester of sorbitan or sorbitol with long-chain fatty acids, and, if appropriate,
c. an amphoteric surfactant,
in aqueous, optionally buffered and salt containing solution. Lauroylsarcosine is preferably used as the amphoteric surfactant.

The invention further provides a composition for the removal of turbidity from biological fluids, which is characterised in that it contains
a. an alkyldimethylbenzylammonium compound,
b. a polyethoxylated triester of sorbitan or sorbitol with long-chain fatty acids, and, if appropriate,
c. an amphoteric surfactant,
in aqueous, optionally buffered and salt containing solution. The composition preferably contains lauroylsarcosine as the amphoteric surfactant.

Inter alia, the composition is suitable for the removal of turbidity in a wide variety of analytical reactions, e.g., for the determination of iron, glucose, magnesium (e.g., by colorometric determination), phosphate (e.g., with ammonium molybdate), etc.

Surprisingly, it has been found that, with the combination of surface-active agents according to the invention, complete and permanent clarification is obtained in well under 10 mintues, even for a proportion or specimen to reagent of 20 vol %. By virtue of the cationic surfactant, the reagent according to the invention is stable, without additional preservatives, at the storage temperatures of 2°–8° C. or 15°–25° C. which are conventionally used for clinicochemical reagents.

Suitable alkyldimethylbenzylammonium compounds are preferably alkyldimethylbenzylammonium chlorides, the alkyl radical being e.g. an unbranched hydrocarbon radical with a chain length of 10 to 14 C atoms. Such compounds are available e.g. under the trademarks Hyamine 3500 from Lonza AG, Basle [Hyamine 3500=n-alkyl (50% $C_{14}$, 40% $C_{12}$, 10% $C_{16}$) dimethylbenzyl ammonium chloride], or Protectol KLC from BASF. Compounds containing branched or aromatic hydrocarbon chains and ether bonds in the alkyl chain, e.g. Hyamine 1622 from Lonza AG, Basle, are also suitable. These compounds are used in aqueous, buffered or non-buffered solution in the pH range from 2 to 12 in a concentration of 0.5 to 10 percent by weight.

Suitable polyethoxylated triesters of sorbitan or sorbitol with long-chain (e.g., $C_{16-20}$, preferably $C_{18}$) fatty acids are polyoxyethylene-20 sorbitan trioleate, e.g., Tween 85 from IC polyoxyethylene-20 sorbitol trioleate, e.g. Witsorbox CO from Witco, or polyoxyethylene-2-0 sorbitan tristearate, e.g. Tween 65 from ICI. These compounds are used in aqueous, buffered or non-buffered solution containing at least one of the alkyldimethylbenzylammonium compounds according to the invention, in the pH range from 2 to 12 in a concentration of 0.5 to 10 percent by weight.

In addition to said cationic and non-ionic surfactants, the composition according to the invention can also contain an amphoteric surfactant, if appropriate. Examples of suitable amphoteric surfactants are amides of sarcosine with carboxylic acids having a chain length of 12 to 14 C atoms, such as N-lauroylsarcosine, e.g. Medialan LD from Hoechst. These compounds are used in aqueous, buffered or non-buffered solution containing at least one of the alkyldimethylbenzylammonium compounds according to the invention and at least one of the non-ionic surfactants according to the invention, in the pH range from 2 to 12 in a concentration of 0.5 to 7 percent by weight.

With the composition according to the invention, clarification takes place within the temperature range of about 15°–37° C. which is conventionally used in clinical chemistry. Buffers which can be used are all the buffers known in clinical chemistry which can maintain a pH range of 2 to 10, preferably phosphate buffer, Tris buffer, PIPES buffer, glycine/HCl buffer etc. The buffer concentration should be in the range from 10 to 200 mmol/l, preferably in the range from 25 to 200 mmol/l.

To increase the ionic strength, the composition according to the invention can also contain a salt, e.g. sodium or potassium chloride in approximately the same concentration as the buffer concentration.

Depending on the analyte to be determined in the biological fluid, the composition can contain further substances for determining this analyte.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above and below, and of corresponding German Published Application 40 18 502, filed Jun. 9, 1990, published Dec. 12, 1991 are hereby incorporated by reference.

Example 1

Reagent for Determining Iron in Serum

| Buffer solution: | |
|---|---|
| | Concentration in the reagent |
| Glycine/HCl buffer, pH 2.9 | 200 mmol/l |
| Guanidinium chloride | 4.5 mol/l |
| Ascorbic acid | 60 mmol/l |
| Hyamine 3500 | 50 g/l |
| Tween 85 | 40 g/l |
| Thiourea | 12 mmol/l |
| Colour reagent: | |
| Glycine/HCl buffer, pH 4.8 | 200 mmol/l |
| 3-(Pyrid-2-yl)-5,6-bis(4-phenyl-sulphonic acid)-1,2,4-triazine disodium salt | 4.8 mmol/l |
| Determination procedure: | |
| Temperature: | 25° C. |
| Wavelength: | 562 nm |
| Path length: | 1 cm |

The following are pipetted into a cell:

| | Analysis | Reagent blank |
|---|---|---|
| Buffer solution | 2.0 ml | 2.0 ml |
| Specimen | 0.4 ml | |
| Double-distilled water | | 0.4 ml |

The solution is mixed, the extinction $E_1$ is measured after 5 minutes, the following is then added:

| | Start reagent | |
|---|---|---|
| | 0.01 ml | 0.01 ml | and the extinction $E_z$ is measured after 3 minutes.

The extinction difference for analysis, $E_A = E_z - E_1$, and the reagent blank, $E_L = E_2 - E_1$, is calculated and the difference $\Delta E = E_A - E_L$ is used to calculate the iron concentration according to the following equation:

$$c = 1195 \times \Delta E \ \mu g/dl$$

Whereas the turbidity of lipaemic sera leads to false results when carrying out the determination without the surfactants according to the invention, an error which cannot even be compensated by measuring a specimen blank, this interference is eliminated up to triglyceride concentrations of 1000 mg/dl or more when using the process according to the invention, depending on the surfactant concentration used.

Example 2

Reagent for determining glucose in serum

| Buffer solution: | |
|---|---|
| | Concentration in the reagent |
| PIPES buffer, pH 7.2 | 50 mmol/l |
| 1-Phenyl-2,3-dimethyl-4-aminopyrazol-5-one | 1 mmol/l |
| Hydroxybenzoic acid | 6 mmol/l |
| Hyamine 3500 | 25 g/l |
| Tween 85 | 25 g/l |
| N-Lauroylsarcosine | 5 g/l |
| Glucose oxidase | 6 kU/l |
| Peroxidase | 3.2 kU/l |
| Mutarotase | 0.05 kU/l |
| Determination procedure: | |
| Temperature: | 25° C. |
| Wavelength: | 500 nm |
| Path length: | 1 cm |

The following are pipetted into a cell:

| | Analysis | Reagent blank |
|---|---|---|
| Buffer solution | 2.0 ml | 2.0 ml |
| Specimen | 0.02 ml | |
| Double-distilled water | | 0.02 ml |

The solution is mixed and the extinction is measured after 5 minutes.

The extinction difference between analysis and reagent blank, $\Delta E = E_A - E_L$, is used to calculate the glucose concentration according to the following equation:

$$c = 342 \times \Delta E \ mg/dl$$

Whereas the turbidity of lipaemic sera leads to false results when carrying out the determination without the surfactants according to the invention, this interference is eliminated up to triglyceride concentrations of 1000 mg/dl or more when using the process according to the invention, depending on the surfactant concentration used.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the removal of turbidity from turbid biological fluids, comprising adding a surface-active agent, wherein the surface-active agent consists essentially of:

a. a $C_{10\text{-}14}$-alkyl-dimethylbenzylammonium compound, and b. a polyethoxylated triester of sorbitan or sorbitol with long-chain fatty acids, in aqueous solution, wherein a. and b. are present in proportions effective to remove turbidity from the fluid.

2. A process of claim 1, said surface active agent further consisting of an amphoteric surfactant.

3. A process of claim 2, wherein the amphoteric surfactant is lauroylsarcosine.

4. A process of claim 1, said surface active agent further consisting of a buffer.

5. A process of claim 1, wherein said surface-active agent further consists of a a salt.

6. A composition for the removal of turbidity from turbid biological fluids, consisting essentially of an aqueous solution of:
   a. 0.5 to 10 percent by weight of a $C_{10\text{-}14}$-alkyl-dimethylbenzylammonium compound, and
   b. 0.5 to 10 percent by weight of a polyethoxylated triester of sorbitan or sorbitol with long-chain fatty acids.

7. A composition of claim 6, further consisting of 0.5 to 7 percent by weight of an amphoteric surfactant.

8. A composition of claim 7, wherein the amphoteric surfactant is lauroylsarcosine.

9. A composition of claim 6, further consisting of 10 to 300 mmol/l of a buffer.

10. A composition of claim 6, wherein said surface-active agent further consists of a salt.

11. In a process for analyzing a turbid biological fluid, the step, prior to the analysis, of removing turbidity of a sample of said biological fluid by adding a composition consisting essentially of an aqueous solution of:
    a. 0.5 to 10 percent by weight of a $C_{10\text{-}14}$-alkyl-dimethylbenzylammonium compound, and
    b. 0.5 to 10 percent by weight of a polyethoxylated triester of sorbitol with long-chain fatty acids.

12. A process of claim 2, said surface active agent further consisting of a buffer.

13. A process of claim 2, said surface active agent further consisting of a salt.

14. A process of claim 12, said surface active agent further consisting of a salt.

15. A composition of claim 7, further consisting of 10 to 300 mmol/l of a buffer.

16. A composition of claim 7, further consisting of a salt.

17. A composition of claim 15, further consisting of a salt.

18. A process according to claim 11, wherein said analysis is conducted photometrically.

19. In a composition for analyzing a turbid biological fluid, wherein the composition consists of analytical reactants, the improvement wherein the composition further consists of a surface-active agent, wherein the surface-active agent consist essentially of:
    a. a $C_{10\text{-}14}$-alkyl-dimethylbenzylammonium compound, and
    b. a polyethoxylated triester of sorbitan or sorbitol with long-chain fatty acids, wherein a. and b. are present in proportions effective to remove turbidity from the fluid.

20. A process of analyzing a turbid biological fluid, the improvement comprises removal of turbidity from a sample of the fluid by the addition of a surface-active agent consisting essentially of:
    a. a $C_{10\text{-}14}$-alkyl-dimethylbenzylammonium compound and
    b. a polyethoxylated triester of sorbitan or sorbitol with long-chain fatty acids,
    in aqueous solution, wherein compound a. and b. are present in proportions effective to remove turbidity from the sample.

21. In a composition for analyzing a turbid biological fluid, wherein said composition consists of analytical reactants, the improvement wherein said composition further consists of a surface-active agent, wherein the surface-active agent consists essentially of an aqueous solution of:
    a. 0.5 to 10 percent by weight of a $C_{10\text{-}14}$-alkyl-dimethylbenzylammonium compound, and
    b. 0.5 to 10 percent by weight of a polyethoxylated triester of sorbitan or sorbitol with long-chain fatty acids.

* * * * *